United States Patent [19]

Ager, Jr.

[11] Patent Number: 4,982,012

[45] Date of Patent: Jan. 1, 1991

[54] TWO PHASE PROCESS FOR PREPARING 2-METHALLYLOXYPHENOL FROM CATECHOL

[75] Inventor: John W. Ager, Jr., Princeton, N.J.

[73] Assignee: FMC Corporation, Philadelphia, Pa.

[21] Appl. No.: 134,641

[22] Filed: Dec. 18, 1987

[51] Int. Cl.$^5$ ............................................. C07C 41/00
[52] U.S. Cl. ................................................... 568/652
[58] Field of Search ........................................ 568/652

[56] References Cited

U.S. PATENT DOCUMENTS

| | | | |
|---|---|---|---|
| 3,474,170 | 10/1969 | Scharpf | 424/285 |
| 3,927,118 | 12/1975 | Ozretich | 568/652 |
| 4,250,333 | 2/1981 | Rakoutz | 568/652 |
| 4,252,985 | 2/1981 | Rakoutz | 568/568 |
| 4,263,462 | 4/1981 | Michelet et al. | 568/652 |
| 4,321,204 | 3/1982 | Buttner et al. | 260/346.22 |
| 4,383,126 | 5/1983 | Buttner et al. | 568/652 |
| 4,390,733 | 6/1983 | Campolini et al. | 568/652 |
| 4,420,420 | 12/1983 | Franko-Filiposie et al. | 568/652 |
| 4,465,868 | 8/1984 | Maekawa et al. | 568/562 |
| 4,542,229 | 9/1985 | Maggioni et al. | 568/652 |
| 4,618,728 | 10/1986 | Hobson et al. | 568/652 |

*Primary Examiner*—Bruce Gray
*Attorney, Agent, or Firm*—Patrick C. Baker; Stanford M. Back; H. Robinson Ertelt

[57] ABSTRACT

2-Methalyloxyphenol is produced selectively in good yield, high purity and without having to separate and recycle large amounts of catechol, in the reaction of methallyl chloride with catechol, by forming a substantially non-aqueous mixture of an alkali metal catecholate and a molar excess of methallyl chloride perferably in a polar organic solvent in which the methallyl chloride is substantially insoluble, agitating the mixture to produce a two-phase system comprising an organic first phase containing product 2-methalyloxyphenol dissolved in methallyl chloride and a polar second phase containing unreacted catecholate, and recovering product 2-methalyloxyphenol from the first plase. The presence of a quaternary ammonium or phosphonium catalyst in the reaction mixture further reduces undesired ring-alkylated by-products.

13 Claims, No Drawings

TWO PHASE PROCESS FOR PREPARING 2-METHALLYLOXYPHENOL FROM CATECHOL

TECHNICAL FIELD

This invention relates to the preparation of 2-methallyloxyphenol by the selective monoetherification of catechol.

BACKGROUND OF THE INVENTION

The monoether 2-methallyloxyphenol (MOP) is useful as an intermediate in the synthesis of benzofuranyl insecticides as disclosed in U.S. Pat. No. 3,474,170. As also described in the patent, MOP is commonly produced by the reaction of methallyl chloride (MAC) with catechol (also known as "pyrocatechol"). However, significant amounts of undesired diether, 1,2-dimethallyloxybenzene, are also obtained. Furthermore, secondary (ring) alkylation reactions also occur, characterized by direct substitution of the methallyl radical onto the aromatic nucleus to form 3-methallylcatechol and/or 4-methallylcatechol. The formation of diether and 4-alkylated derivatives reduces the yield of the desired monoether (MOP) and results in a mixture of compounds from which it is difficult and expensive to isolate the monoether.

Formation of undesirable amounts of by-products is commonly controlled by the use of a large excess of catechol and by limiting catechol conversion. However, this process is inefficient and uneconomical because it requires recovery and recycling of large proportions of the catechol charge, typically about 50%. In another process, described in U.S. Pat. No. 4,252,985, methallyl chloride is reacted with catechol in the presence of a basic agent and a catalyst, using a stirred, two-phase liquid reaction medium comprising water and a water-immiscible, inert organic solvent. The catalyst is a quaternary ammonium or phosphonium derivative. The preferred organic solvent is anisole, although methallyl chloride can act as both the reactant and the water-immiscible solvent. Despite the benefit of selective mono-etherification, the reaction is complicated by the aqueous phase because unreacted catechol collects therein as well as in the anisole phase and must be extracted for later recovery and recycling. Moreover, some of the catechol remains in the product MOP, thereby requiring further purification.

SUMMARY OF THE INVENTION

It has now been found, in one aspect of the invention, that 2-methallyloxyphenol (MOP) can be produced with improved purity and high yield in an uncatalyzed, substantially anhydrous two-phase reaction system by the reaction of a molar excess of methallyl chloride (MAC) with a catecholate, the reaction system optionally, but preferably, containing a polar organic solvent.

In another aspect of the invention, high purity 2-methallyloxyphenol is produced (in some cases on the order of 80–85% on a solvent-free basis) in an anhydrous, two-phase reaction system by the reaction of a molar excess of methallyl chloride with a catecholate in the presence of a quaternary catalyst, the reaction system optionally, but preferably, containing a polar organic solvent.

In a preferred anhydrous two-phase etherification reaction of the present invention, a substantially non-aqueous mixture of catechol, base and a polar organic solvent (in which MAC is substantially insoluble) is formed. The mixture is then combined with a molar excess of MAC with agitation, whereupon the mixture separates into two phases: an upper, organic first phase comprising product MOP dissolved in excess MAC, and a lower, polar (hydrophilic) second phase comprising unreacted catechol, base and solvent. More preferably, a quaternary catalyst is added to the initial mixture or during the agitation. Because the product MOP has greater solubility in the methallyl chloride phase, it may be continuously extracted as formed, thereby reducing the opportunity for secondary (ring) alkylation and facilitating recovery of the product.

The process of the invention thus produces the desired monosubstituted ether in high yield (based on conversion of catechol) and with high purity, and avoids the inconvenience and expense of recovering substantial quantities of catechol as in prior processes.

DETAILED DESCRIPTION

As indicated above, the process of the invention takes place in a substantially anhydrous reaction medium. It will be appreciated, however, that as in reactions of most organic compounds wherein a base is present, particularly as an alkali metal compound, some water will be in the system. Water in substantial amounts in the process of the present invention is undesirable because it contaminates the polar phase, requiring additional processing to separate and to purify the product. Water may be eliminated entirely, or at least further reduced, by preforming the catecholate (by reaction of catechol and an alkali metal compound in a mole ratio of about 1:2 to 2:1) and/or by refluxing the water out of the system as it is formed. Some water can be tolerated in the second, polar phase, but amounts of water sufficient to form a separate, aqueous phase should be avoided.

The substantially anhydrous character of the process optimizes the effect of the relative solubilities of the reactants and product, since the product MOP is soluble in the MAC but unreacted catechol is not. Consequently, the catechol forms a separate phase or, stated another way, remains behind in the pot as the product MOP separates into the top phase. The MOP is then recovered, as by decanting, followed by stripping off of MAC.

In one mode of practice of the process, a substantially non-aqueous mixture of an alkali metal catecholate and a molar excess of MAC is formed. The amount of MAC is sufficient to provide an easily stirrable slurry, e.g., at least 5 moles of MAC per mole of catecholate, preferably a mole ratio of about 10:1 to 20:1 or more, most preferably about 10:1 to 15:1. The mixture is then agitated, such as by stirring. The upper, organic phase comprises product MOP dissolved in MAC. The second (lower) polar phase comprises the remaining reagents.

In another mode of practice, an inert, polar organic solvent is added to the reaction mixture to operate as the primary reaction medium. Suitable organic solvents are those in which the MAC is substantially insoluble. Such solvents include polyhydroxy organic compounds, preferably containing 2 to 5 carbon atoms, of which alkylene glycols, glycol ethers, and certain tri, tetra and penta hydroxy compounds are representative. Suitable solvents of this class include ethylene glycol, diethylene glycol, propylene glycol, glycerol, pentaerytritol, and the like, including mixtures thereof.

If the catecholate is to be formed in situ by reaction of an alkali metal base and catechol, it is convenient to disperse the base in the organic solvent, and then add catechol. The resulting mixture may then be combined with the MAC in any suitable manner, preferably by adding the mixture to the MAC with agitation.

Suitable bases for use in the process include any basic alkali metal compounds such as alkali metal carbonates, bicarbonates, hydroxides and methylates, including any mixture thereof. Sodium and potassium are the preferred alkali metals and sodium carbonate and bicarbonate are the preferred bases. The base is added in at least equimolar amounts with respect to catechol, but preferably in molar excess, e.g., 10% to 50% excess, in order to assist in driving the reaction to completion. Of course, if the catecholate is preformed, a lesser amount of alkali metal base will be effective than in the case of forming the catecholate in situ.

In a further mode of practice of the process of the invention, a quaternary catalyst is added to, or produced in situ in, the reaction mixture prior to or in conjunction with formation of the two phases. The quaternary catalyst may be formed in situ by addition to the mixture of an amino compound capable of quaternizing with MAC. Suitable amino compounds are liquid amines including alkylamines such as trialkyl ($C_1$–$C_4$) amines, e.g., triethylamine, and N-heterocyclic amines such as pyridine and quinoline. If the catalyst is preformed and added separately, suitable catalysts are the well-known quaternary ammonium and phosphonium phase transfer catalysts such as described in U.S. Pat. No. 4,252,985, the disclosure of which is incorporated herein by reference. Another quaternary catalyst is methallyl pyridinium chloride, which may be formed in situ from pyridine in the presence of MAC.

The catalyst is employed in a catalytically effective amount, e.g., from about 0.01 to about 1.0 mole per equivalent of catechol or catecholate in the reaction mixture, preferably about 0.1 to about 0.25 mole on the same basis. Mixtures of quaternary salts can also be used as the catalyst. The catalyst helps to reduce or eliminate formation of ring-alkylated by-products. However, when the catalyst is formed in situ by addition to the reaction mixture of an amino compound, it is preferred to include a polar organic solvent in the reaction mixture because amino compounds tend to form pasty mixtures. Such mixtures are more difficult to handle than the more fluid mixtures obtained with polar organic solvents.

The reactants and other reagents of the process, including the catalyst, may be added in any sequence and either incrementally or all at once, with the exception that conditions should be selected such that catechol or catecholate is never present in excess with respect to MAC, in order to avoid or minimize dietherification. Preferably, the catechol or catecholate is added incrementally to the methallyl chloride.

Any combination of temperature and pressure effective for controlled reaction can be used. In an open system, room temperature to reflux (about 130° C.) is suitable. In a pressurized or autogenous reactor, reaction temperature can be higher, depending on the pressure. Reaction time can vary considerably, depending on the solvent system, temperature and pressure, and whether or not a catalyst is used. Generally, a reaction time of about 1–5 hours for an atmospheric pressure process is suitable.

An oxygen scavenger, such as sodium dithionite, may be added to the reaction mixture to prevent oxidation of the catechol or catecholate. The reaction preferably is conducted in an inert atmosphere for the same purpose.

As the phases form and separate in the reaction mixture, the MOP product is conveniently recovered by decanting and then distilling off the residual MAC in the MOP. The product MOP may be further purified in a known manner, if desired. As indicated above, the success of the process depends on the substantially anhydrous reaction medium and relative solubilities of the reactants and reagents. By maintaining MAC in large excess with respect to catechol, the unreacted catechol (which is insoluble in MAC) concentrates in a phase (polar) separate from the MOP product phase. Concentration in a separate phase is also promoted by alkali metal base in the reaction mixture because the resulting catecholate is insoluble in MAC. Accordingly, the small amount of remaining unreacted catechol is easily removed from the reaction mixture, following recovery of the MOP product, thereby avoiding the inconvenience and expense of recovery of large amounts of catechol from an aqueous phase as in the process of U.S. Pat. No. 4,252,985.

The process of the invention makes it possible to achieve, simultaneously, at least 50% conversion of catechol and a product purity of more than 85%. In some cases 80% or more catechol conversion is obtained.

The following examples further illustrate the invention but are not intended to limit the scope thereof. Examples 1–4 are uncatalyzed etherifications. Examples 5–7 represent catalyzed etherifications of the invention. In the Examples all parts and percentages are by weight unless otherwise indicated.

EXAMPLE 1

A mixture of 25 g catechol, 25 g sodium carbonate, 250 g anhydrous glycerol and 250 g MAC was stirred and heated for 30 minutes at 60° C. The MAC layer was decanted. To the glycerol layer was added another charge of 25 g catechol, 25 g sodium carbonate and 250 g MAC. After 20 minutes at 60° C., the MAC layer was decanted. 250 g of fresh MAC was added, heated and decanted. This step was repeated to give 5 MAC treatments of this second charge of catechol in sodium carbonate to make a total of 6 MAC treatments in all. The last 5 MAC extracts were combined and distilled to give 75 g of residue which was dissolved in 100 ml toluene and washed with water to remove glycerol. GC analysis of the residue indicated a yield of approximately 58% MOP and approximately 100% conversion of catechol.

EXAMPLE 2

A mixture of 50 g catechol, 2.5 g sodium methoxide, 200 g MAC and 100 g anhydrous glycerol was stirred vigorously and heated at 60 to 70° C. for 15 minutes. After decanting the MAC layer, another 200 g of MAC was added and the mixture was heated and stirred. The MAC layer was decanted and a third 200 g charge of MAC was added. The mixture was heated and stirred for 30 minutes at 70°–75° C. The MAC layer was decanted for a third time and a fourth 200 g charge of MAC was added. The mixture was stirred vigorously and heated at 70 to 75° C. The MAC layers were combined, washed with water and distilled to yield 46.2 g of liquid having a catechol conversion of approximately 60% and area purity of approximately 66%.

EXAMPLE 3

A mixture of 10 g catechol, 9.3 g potassium carbonate, 40 g ethylene glycol and 300 g MAC was refluxed at 70° C. for 30 minutes. The MAC layer was decanted and stripped on a rotary evaporator to give 14 g of liquid which was approximately 77% MOP. Catechol conversion was approximately 98%.

EXAMPLE 4

A mixture or 20 g catechol, 13 g potassium carbonate, 40 g ethylene glycol and 300 g MAC was heated at 50–55° C. for 1½ hours. The MAC layer was decanted and stripped to give 4.9 g of liquid which was approximately 91% MOP and 2.4% catechol on a solvent-free basis. To the glycerol layer was added a second 300 g of MAC and the mixture was heated at 50°–60° C. for 1½ hours. Decanting and stripping gave 7.3 g of liquid which was 82% MOP and 5% catechol on a solvent-free basis. The combined MAC charges yielded approximately 85% catechol conversion and 85% MOP purity.

EXAMPLE 5

A mixture of 10 g catechol, 10.8 g pyridine, 300 g MAC and 7.6 sodium bicarbonate was stirred vigorously for 2 hours. The MAC was decanted, washed with water and stripped to give 10.9 g of liquid which was 90% MOP and 8% diether. To the thick residue left after the MAC layer was decanted was added 10 g catechol, 7.6 g sodium bicarbonate and 300 g MAC. This mixture was refluxed for one hour. The MAC was decanted and stripped to give 11 g of liquid which assayed 74% MOP. This process was repeated and the MAC layer decanted after one hour. To the thick pot residue was then added an additional 300 g MAC (without additional catechol or carbonate). This mixture was refluxed for two hours, decanted and stripped to give 9 g of liquid which was 78% weight MOP. In this experiment, catechol conversion was approximately 70% and MOP yield was approximately 90%.

EXAMPLE 6

A mixture of 40 g ethylene glycol, 7.1 g pyridine and 20 g MAC was heated at 80° C. for about one hour, until the odor of pyridine had dissipated. To the mixture was added 7.6 g sodium bicarbonate and the resultant mixture was heated at 80° C. for 90 minutes. 10 g catechol was then added and the mixture was stirred until carbon dioxide evolution had ceased. The mixture was refluxed for 90 minutes, the MAC decanted and stripped. The product was 11.2 g of liquid which assayed 80% MOP and 2.5% catechol.

To the residue left after decanting of the MAC layer was added 10 g catechol, 5.8 g sodium bicarbonate and 300 g MAC. After refluxing for 30 minutes the MAC layer was decanted and stripped down to give 14.4 g product which assayed 80 wt % MOP and 3.3 wt % catechol. To the pot residue was added 10 g catechol, 5.8 g sodium carbonate and 150 g of MAC. After 30 minutes reflux the MAC was decanted and stripped to give 14.1 gram of liquid which assayed 76 wt % MOP and 4.6 wt % catechol. To the pot residue was added 40 g water, 5.8 g (0.055 mole) sodium carbonate and 300 g MAC. After 30 minutes reflux, the MAC was decanted and stripped to give 11.1 g of liquid which assayed 66 wt % MOP and 5.8 wt % catechol.

EXAMPLE 7

A mixture of 7.1 g (0.09 mole) pyridine in 300 g MAC was refluxed overnight. The product was a yellow liquid which crystallized upon cooling. The MAC layer was decanted, and to the crystallized product was added 7.4 g (0.09 mole) sodium bicarbonate, 50 ml methanol and a small amount of water. When this mixture was heated, carbon dioxide evolved. After carbon dioxide evolution ceased, the mixture was stripped at reduced pressure and yielded 20 g of residue. To the residue was added 40 g ethylene glycol, 10 g catechol and 300 g MAC. After one hour at reflux, the MAC was decanted, washed and stripped to give 11.4 g liquid which assayed 80 wt % MOP and 3.5 wt % catechol. This is approximately 78% conversion.

I claim:

1. A process for increasing the yield and purity of 2-methallyloxyphenol, produced by the reaction of methallyl chloride and catechol, which process comprises:
    (a) forming a substantially non-aqueous mixture of an alkali metal catecholate and a molar excess of methallyl chloride;
    (b) agitating the mixture to produce a two-phase system comprising an organic first phase containing product 2-methallyloxyphenol dissolved in methallyl chloride and a polar second phase containing unreacted catecholate; and
    (c) recovering product 2-methallyloxyphenol from the first phase.

2. The process of claim 1 wherein the mixture additionally contains a polar organic solvent.

3. The process of claim 2 wherein the polar organic solvent comprises a polyhydroxy organic compound.

4. The process of claim 3 wherein the polyhydroxy compound is selected from at least one of glycerol, ethylene glycol and propylene glycol.

5. The process of claim 1 wherein the mixture additionally contains an amino compound in an amount effective to form a catalyzing quaternary salt with excess 2-methyallyl chloride.

6. The process of claim 5 wherein the amino compound is triethylamine or pyridine.

7. The process of claim 1 wherein the mixture additionally contains a polar organic solvent and a preformed quaternary catalyst in an amount effective to catalyze said reaction.

8. The process of claim 1 further including adding a quaternary catalyst to said mixture in step (a) or during agitation in step (b) in an amount effective to catalyze said reaction.

9. The process of claim 8 wherein the quaternary catalyst is selected from quaternary ammonium and quaternary phosphonium compounds.

10. The process of claim 1 wherein the alkali metal catecholate is formed in situ in the mixture by the reaction of catechol and a basic alkali metal compound.

11. The process of claim 10 wherein the alkali metal compound is selected from an alkali metal carbonate, bicarbonate, hydroxide and methylate.

12. The process of claim 1 wherein the mole ratio of methallyl chloride to catecholate is at least about 5:1.

13. The process of claim 1 wherein the mole ratio of methallyl chloride to catecholate is at least about 10:1.

* * * * *